(12) United States Patent
Salman et al.

(10) Patent No.: US 7,567,086 B2
(45) Date of Patent: Jul. 28, 2009

(54) METHOD AND ARTICLE OF MANUFACTURE FOR MONITORING STATE OF HEALTH OF AN ELECTRICAL ENERGY STORAGE DEVICE

(75) Inventors: Mutasim A. Salman, Rochester Hills, MI (US); Mark W. Verbrugge, Troy, MI (US); Zhenhui Yao, Warren, MI (US)

(73) Assignee: GM Global Technology Operations, Inc., Detroit, MI (US)

( * ) Notice: Subject to any disclaimer, the term of this patent is extended or adjusted under 35 U.S.C. 154(b) by 241 days.

(21) Appl. No.: 11/561,907

(22) Filed: Nov. 21, 2006

(65) Prior Publication Data

US 2007/0132456 A1  Jun. 14, 2007

Related U.S. Application Data

(60) Provisional application No. 60/748,889, filed on Dec. 9, 2005.

(51) Int. Cl.
*G01N 27/416* (2006.01)
(52) U.S. Cl. .................................... 324/426
(58) Field of Classification Search ................ 324/426, 324/427, 430, 433; 320/107, 132, 141, 162
See application file for complete search history.

(56) References Cited

U.S. PATENT DOCUMENTS

| | | |
|---|---|---|
| 4,937,528 A | 6/1990 | Palanisamy |
| 6,417,646 B1 * | 7/2002 | Huykman et al. ........... 320/122 |
| 6,445,158 B1 | 9/2002 | Bertness |
| 6,885,167 B2 | 4/2005 | Palanisamy |

OTHER PUBLICATIONS

Verbrugge,M., Adaptive Energy Mgt. of Electric & Hybrid Electric Vehicles, J. Electrochemical Society, 2005, 152(2), Electrochemical Soc., Pennington, NJ, US.
Cox,M., Auto 'Smart' Battery with SOH Conductance Testing and Monitoring Technology, 2003, SAE Tech Paper Series, 2003-01-0099, SAE, Warrendale, PA, USA.
Verbrugge,M.,Adaptive SOC Algorithm for Ni-Metal Hydride batteries including hysteresis Phenomena, 2004, J. of Power Sources, 126(2004) 236-249, Elsevier, www.Elsevier.com.
Verbrugge,M., Generalized Recursive Algorithm for Adaptive Multiparameter Reg. Appln. to Pb-, Ni-MH, and Li- Batteries, 2006, J. Electrochemical Society, 153(1).
Electrochemical Society, Pennington, NJ US, dated 2005.

* cited by examiner

*Primary Examiner*—Edward Tso

(57) ABSTRACT

There is provided a method and article of manufacture for monitoring an electrical energy storage device for a system. The method comprises stabilizing the electrical energy storage device. Once the device is stabilized, a discrete electrical load is cyclically applied to the electrical energy storage device and state variables of the electrical energy storage device are monitored. A resistance of the electrical energy storage device is determined, and a remaining useful life parameter of the electrical energy storage device is determined based upon the determined resistance.

20 Claims, 4 Drawing Sheets

Battery Current Measurements

METHOD AND ARTICLE OF MANUFACTURE FOR MONITORING STATE OF HEALTH OF AN ELECTRICAL ENERGY STORAGE DEVICE

CROSS-REFERENCE TO RELATED APPLICATIONS

This application claims the benefit of U.S. Provisional Application No. 60/748,889 filed Dec. 9, 2005, entitled METHOD AND APPARATUS FOR MONITORING AN ELECTRICAL ENERGY STORAGE DEVICE.

TECHNICAL FIELD

This invention pertains generally to electrical energy storage devices, and more particularly to a method and apparatus to determine a state of health of such devices.

BACKGROUND OF THE INVENTION

Modern vehicles are highly dependent on proper operation of systems used for electrical power generation, storage and distribution. There is a need for a reliable supply of electrical energy to operate various systems on-board each vehicle. Consistent power output from an electrical energy storage device, such as a battery, is critical for maintaining the vehicle operation. Battery problems lead to service issues and customer dissatisfaction. Therefore, there is a need to monitor ability of a battery to deliver power throughout its life. Reliable electrical power supply is critical for vehicle operation, especially in newer vehicle systems that depend on electrical power, such as x-by-wire systems and hybrid powertrain systems. Systems which monitor electrical current and voltage during engine operation are typically noisy, making it difficult to extract battery operating parameters. Furthermore, in the event of a system fault, service personnel benefit from being able to isolate faults to effectively repair a vehicle electrical system.

Therefore, there is a need for a monitoring system for an electrical storage device that addresses the aforementioned concerns.

SUMMARY OF THE INVENTION

In accordance with an embodiment of the invention, there is provided a method for monitoring an electrical energy storage device for a system. The method comprises stabilizing the electrical energy storage device. Once the device is stabilized, a discrete electrical load is cyclically applied to the electrical energy storage device and parameters of the electrical energy storage device are monitored. A resistance of the electrical energy storage device is determined, and a remaining useful life parameter of the electrical energy storage device is determined based upon the determined resistance.

These and other aspects of the invention will become apparent to those skilled in the art upon reading and understanding the following detailed description of the embodiments.

BRIEF DESCRIPTION OF THE DRAWINGS

The invention may take physical form in certain parts and arrangement of parts, an embodiment of which is described in detail and illustrated in the accompanying drawings which form a part hereof, and wherein.

DETAILED DESCRIPTION OF AN EMBODIMENT OF THE INVENTION

Figure 1:
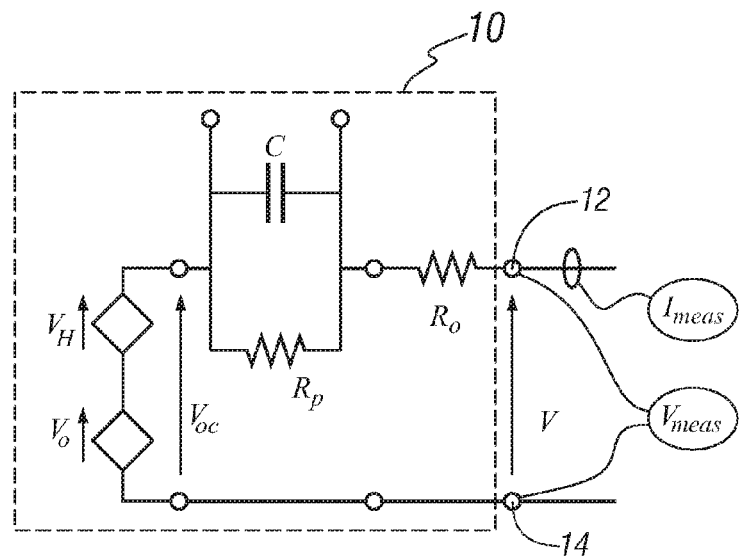
FIG. 1 is a schematic diagram of an exemplary electrical circuit, in accordance with the present invention.

Referring now to the drawings, wherein the showings are for the purpose of illustrating the invention only and not for the purpose of limiting the same, FIG. 1 depicts a schematic diagram comprising a Thevenin equivalent circuit representative of an exemplary ESD 10, in accordance with an embodiment of the present invention. The equivalent circuit comprises voltage generating elements Vo and $V_H$, and internal impedance elements comprising high frequency resistance Ro, parallel resistance Rp, and parallel capacitance C. There is an open-circuit potential Voc, and an electrical energy output measurable across terminals 12, 14 comprising a voltage V, and an electrical current.

The invention comprises a method for monitoring parameters of the electrical energy storage device (ESD) 10 for a system to determine a state of health, i.e., predict a remaining useful life for the ESD, by estimating internal resistance of the ESD under specific operating conditions. The ESD can be a battery device for application in a vehicle, including e.g., a battery device operative to supply electrical energy to an electro-mechanical hybrid vehicle system. The method is preferably executed as an algorithm in one or more electronic control modules, comprising cyclically applying a load in form of an electrical discharge current to the battery as a waveform, e.g., a square wave. The discharge current waveform is applied to the battery at varying cycle periods, or frequencies. The load is preferably applied to the system after shut down or deactivation for an elapsed period of time of sufficient duration to permit temperature stabilization. Alternatively, the load can be applied to the system during system operation when stabilized conditions occur.

The load waveform is preferably of a duty cycle and power consumption sufficient to excite the circuit to accurately estimate battery parameters, including the high frequency resistance Ro. Determining a change in the high frequency resistance from a baseline high frequency resistance results in a measure of battery state of health (SOH), and is depicted with reference to FIG. 5. A change in SOH over service life of the battery enables assessment of irreversible losses due to aging. The battery high frequency resistance is repeatedly estimated and stored as a function of ambient temperature. A normalized difference between the parameter for high frequency resistance and a limiting value at the same temperature is indicative of battery remaining useful life. An exemplary limiting value comprises a resistance value at which the battery is no longer capable of producing enough power to start the vehicle. An embodiment of the method is now described in detail with reference to the figures.

Referring again to FIG. 1, the circuit 10 depicts estimated internal battery parameters comprising high frequency resistance Ro, parallel resistance Rp, parallel capacitance C, and open circuit voltage Voc.

The equations described herein and executed in parametric identification are based on the circuit in FIG. 1. An equation representative of the circuit is in Eq. 1, below:

$$V(i)+\theta_1 V(i-1)=\theta_2 \cdot 1+\theta_3 I_L(i)+\theta_4 I_L(i-1) \qquad [1]$$

wherein state variables V(i) and $I_L(i)$ comprise terminal voltage and load current measured at the output terminals 12, 14 of the battery 10, at sample time point (i), i.e., $V_{meas}$ and $I_{meas}$. State variables V(i−1) and $I_L$(i−1) comprise the terminal voltage and the load current measured at a previously occurring sample point (i−1), occurring at elapsed time Δt. Estimated parameters are determined, as described in Eqs. 2 through 6, wherein:

$$\theta_1 = -e^{-\frac{\Delta t}{\tau}} \quad [2]$$

$$\theta_2 = (1 - e^{-\frac{\Delta t}{\tau}})V_{OC} \quad [3]$$

$$\theta_3 = -\left(R_O + \frac{\Delta t}{2C}\right) \quad [4]$$

$$\theta_4 = \left(R_O - \frac{\Delta t}{2C}\right)e^{-\frac{\Delta t}{\tau}} \quad [5]$$

and, $$\tau = R_P C \quad [6]$$

and, wherein the estimated battery parameters comprise high frequency resistance Ro, parallel resistance Rp, parallel capacitance C, and open circuit voltage Voc of the ESD, as shown in FIG. 1.

Based on the estimated parameters, parametric values for the circuit elements can be estimated using Eqs. 7, 8, 9, and 10, as follows:

$$V_{OC} = \frac{\theta_2}{1 + \theta_1} \quad [7]$$

$$R_O = \frac{1}{2}\left(-\frac{\theta_4}{\theta_1} - \theta_3\right) \quad [8]$$

$$C = \frac{-\Delta t}{2(R_O + \theta_3)} \quad [9]$$

$$R_P = \frac{-\Delta t}{C\ln(-\theta_1)} \quad [10]$$

Eq. 1 and Eqs. 2-10 are preferably executed recursively during application of the aforementioned cyclically applied external electrical load to determine parametric values for Ro, Rp, C, and Voc, which converge with time.

The resistances Ro and Rp comprise high frequency and low frequency resistances, which are indicators of battery aging. High frequency resistance Ro is independent of battery state of charge (SOC) for values above 60% while Rp is indicative of SOC. Both resistances typically vary as a function of ambient temperature. The high frequency resistance, Ro, can be used as an indicator of aging because it is independent of SOC, and therefore a more stable parameter to estimate.

Parametric values for high frequency resistance Ro typically vary between battery devices. Therefore, baseline values of Ro, as a function of temperature, are preferably generated for each battery during initial operation in the system. When a new battery is installed as part of a new system, or as a retrofit or service part for an existing system, the values of estimated high frequency resistance Ro as a function of temperature are stored in a calibration table stored in the control module during in-use service of less than a calibrated number of cycles or weeks, and a remaining life time indication of 100% is communicated to the vehicle operator. The collected measurements of battery voltage and current are executed in a recursive least square (RLS) algorithm to identify the battery parameters as described in the electric circuit.

Figure 2:
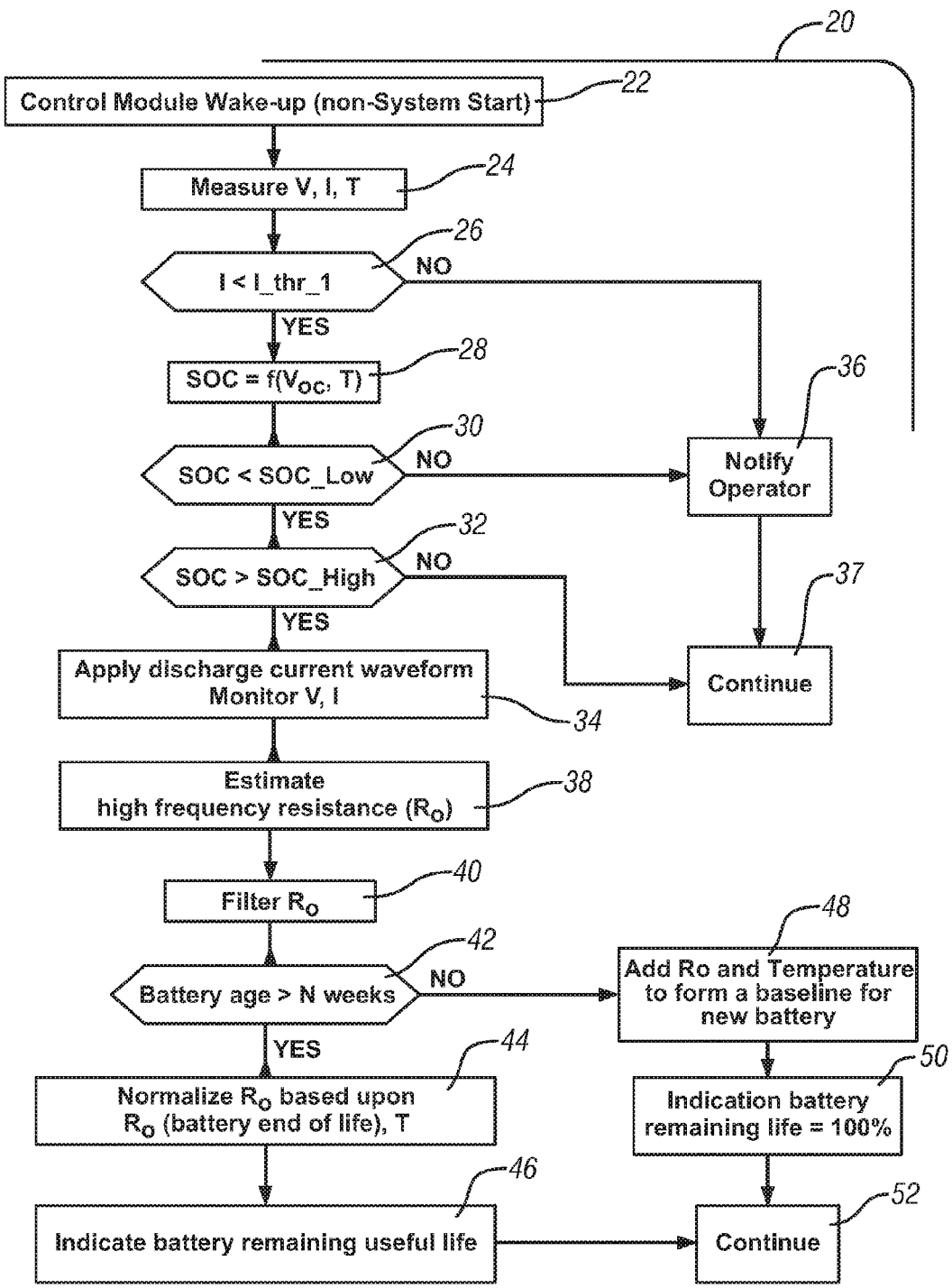
FIG. 2 is a diagram of an algorithmic flowchart, in accordance with the present invention; and, FIGS. 3, 4, and 5 are data-graphs, in accordance with the present invention.

Referring now to FIG. 2, a flow chart is depicted for an algorithm 20, preferably executed in the control module, for determining a SOH prognosis of an exemplary ESD for a system, including recursive execution of Eqs. 1-10 effective to determine a parametric value for high frequency resistance, Ro. In this embodiment, the exemplary system is preferably shut-off for at least a predetermined period of time sufficient to stabilize various battery characteristics, particularly temperature. System shut-off comprises a key-off period when the system is implemented on a vehicle. After the predetermined period of time after system shutdown has elapsed, the control module is activated, or wakes up, but the overall system is not activated (Step 22). The control module operates to obtain readings from sensors, effect cyclic actuation of a load device, and execute machine code comprising one or more algorithms to determine battery parameters, as described herein. The control module takes readings of state variables comprising open circuit battery voltage Voc, current I, and, battery temperature T (Step 24). Battery voltage and current are measured using known sensors and signal processing algorithms. It is preferable to have a measure of battery temperature determined using a sensor, or, alternatively using a battery temperature estimator. Battery current I is compared to a first threshold, I_Thr_1 (Step 26). When the battery current is less than the first threshold current, the measured voltage is regarded as the same as an open-circuit voltage, i.e., Voc=Vmeas (Step 26). Under this condition, battery state-of-charge (SOC) can be determined from a calibrated look-up table stored in the control module. The calibrated look-up table comprises using the battery open-circuit voltage Voc and battery temperature T to determine the battery SOC, i.e., SOC=f(Voc, T) (Step 28). When the battery current is greater than the first threshold, then a battery leakage current is present, which can be due to a vehicle load that is left on or an electrical system fault. The control module sends a warning message to the vehicle operator regarding the high leakage current (Step 36). Thus, when the battery current is greater than the first threshold current, I_thr_1, a warning is sent to the operator and the algorithm ends operation (Step 37).

When the battery SOC is determined (Step 28), it is compared to a low threshold SOC_Low (Step 30) and an upper threshold SOC_High (Step 32). When the SOC is less than the low threshold value (e.g., 50% SOC), a warning is sent to the operator (Step 36). When SOC is greater than the low threshold but less than the upper threshold (e.g. 70%), no further action is taken, i.e., a discharge current is not applied at this time (Step 37). When the SOC is larger than the upper threshold, a discharge current, or load, is cyclically applied across the terminals of the ESD and battery voltage V and current I are monitored during the applied load (Step 34).

The cyclically applied load comprises applying a plurality of cycles of an appropriate discharge current having varying cycle time periods across the terminals 12, 14 of the ESD 10. Generating the cyclical load to the electrical energy storage device comprises cyclically activating and deactivating a discrete electrical load, and can be in the form of a square waveform, with the waveform comprising a series of recurring high load events and no-load events. The cyclical load waveform preferably comprises a plurality of cycles having frequencies successively increasing during the load event, i.e., decreasing a cycle period of activating and deactivating the discrete electrical load. Preferably a plurality of successive cyclical electrical load events are executed, wherein each cyclical load event comprises a plurality of cycles of the discrete electrical load applied at a fixed frequency, and each successive cyclical electrical load event is executed at an increased frequency. To implement the current waveform, the control module repetitively actuates and deactivates a discrete electrical load. An exemplary load for a typical system ranges between about 15 amps to 30 amps. An example of a discrete electrical load is a vehicle rear window defogger.

Figure 3A:
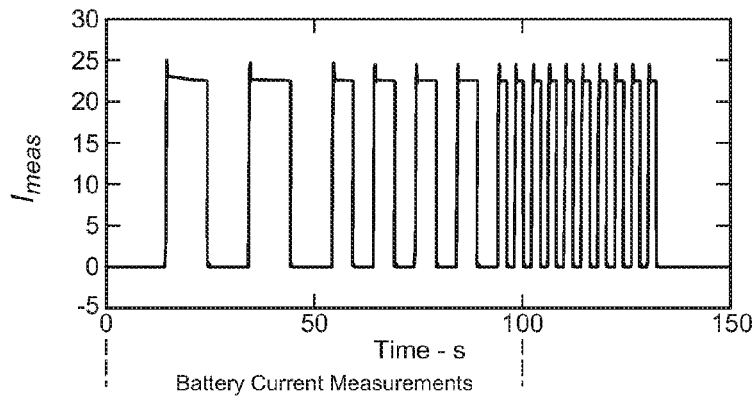
Figure 3B:
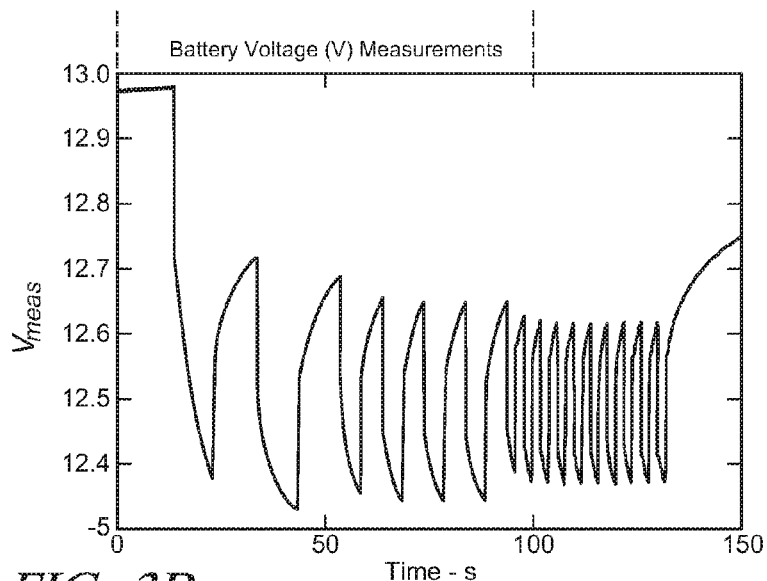
Figure 4:
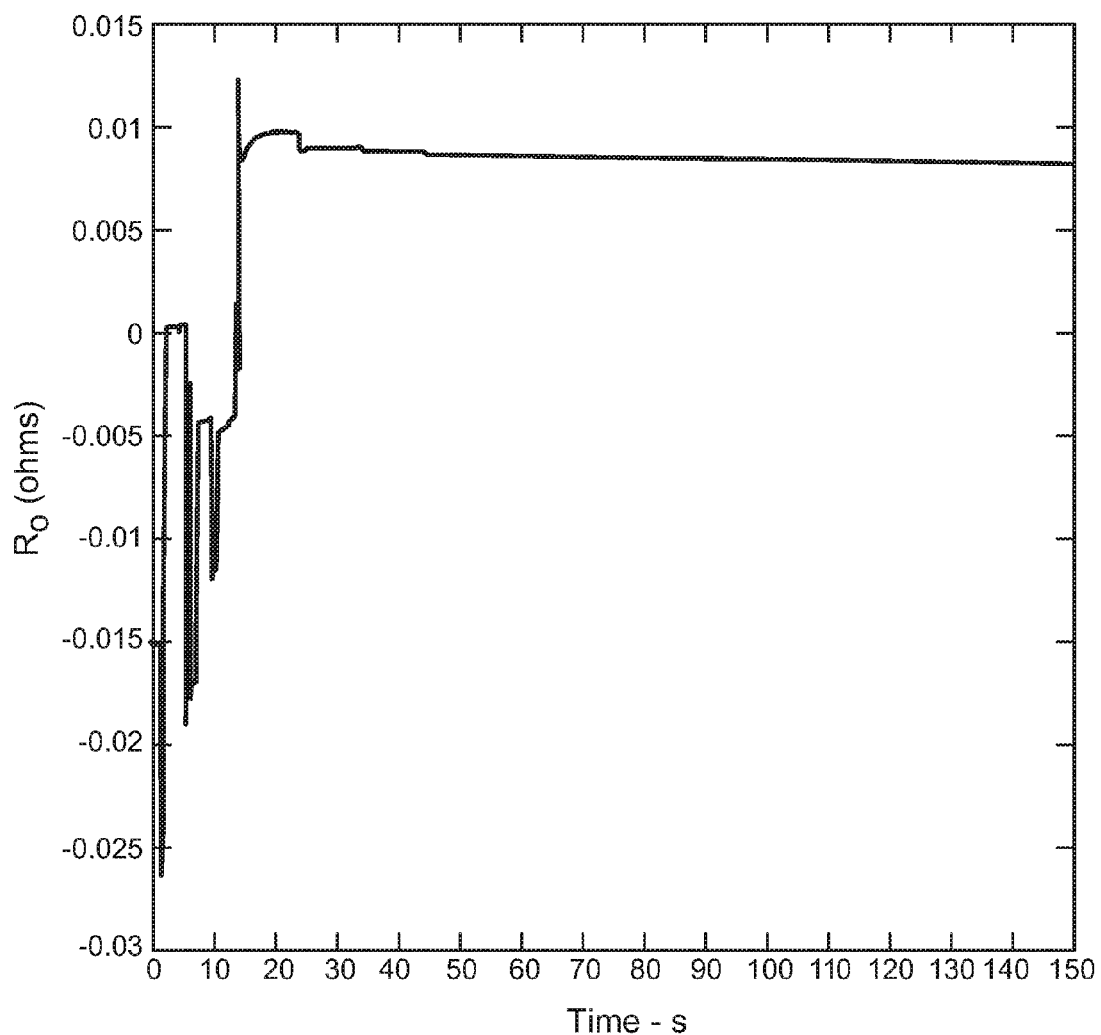

Referring now to FIGS. 3A and 3B, an exemplary applied load in accordance with the invention is depicted, in terms of electrical current (FIG. 3A) and electrical voltage (FIG. 3B). Total duration of the cyclically applied load is about 120 seconds for this illustration. Frequencies and duration of the cyclically applied load are application-specific, preferably selected to effectively determine high frequency resistance of the ESD, and based upon ESD design, system operating conditions, and other factors. The exemplary load is applied in three segments at varying frequencies. Each segment has a duration of about 40 seconds, each having a 50% duty cycle. The first segment has two cycles; each with a period of 20 seconds (10 seconds load on and 10 seconds load off). The second segment has four cycles; each with a period of 10 seconds (5 seconds on and 5 seconds off). The third segment has 10 cycles; each with a period of 4 seconds (2 seconds on and 2 seconds off). During operation, state variable data are collected from the system, i.e., $V_{meas}$ and $I_{meas}$, and the equations above, i.e., Eq. 1-10, are executed recursively by one or more algorithms in the control module, to determine parametric values for Voc, Ro, C, Rp (Step 38). An exemplary determination of high frequency resistance, Ro, calculated and estimated recursively using the Eqs. 1-10, is depicted in FIG. 4, wherein a stabilized value is reached after about 30 seconds of the recursive operation.

Figure 5:
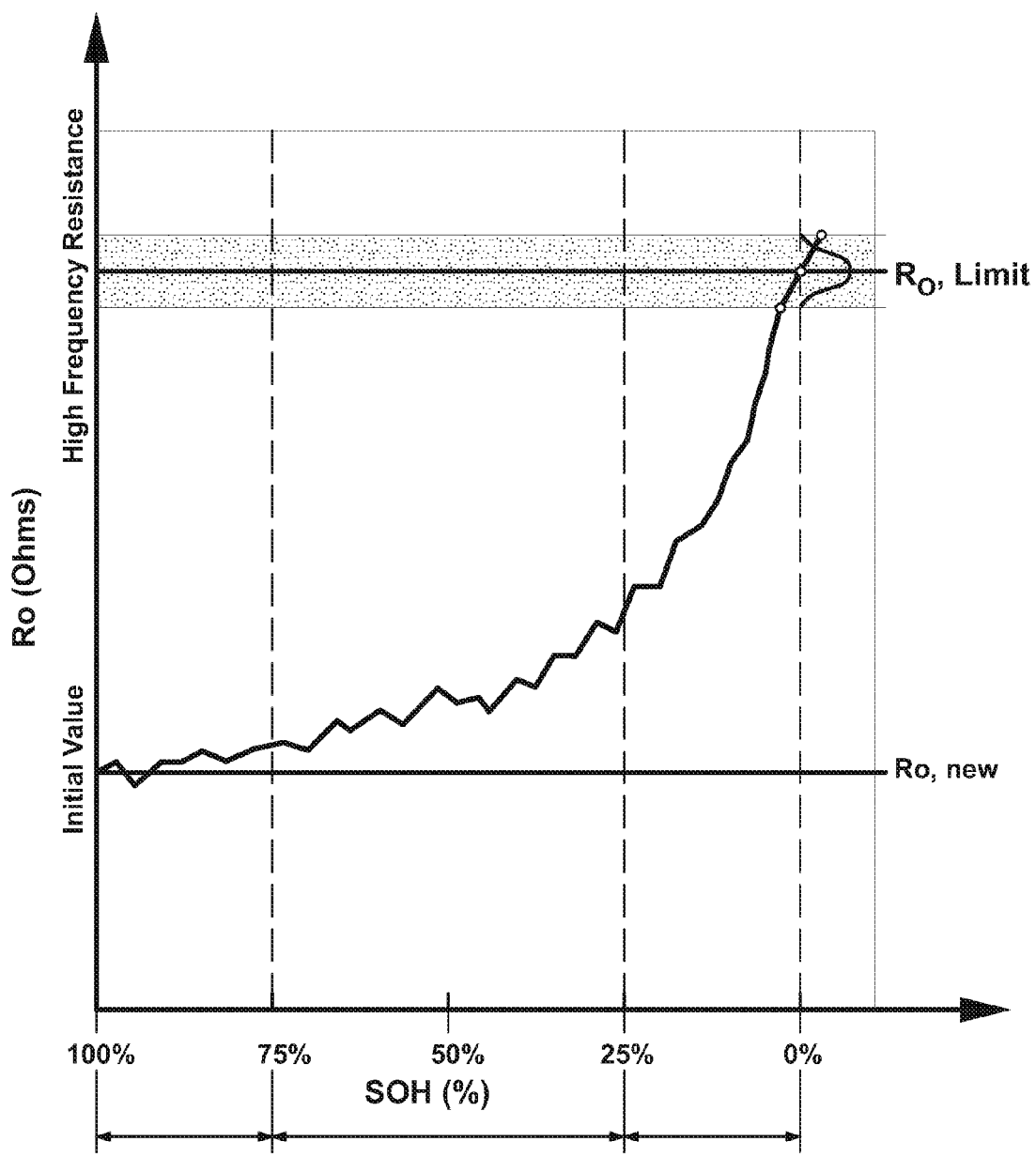

As the battery ages from ongoing cyclical charging and discharging, the high frequency resistance, Ro, increases due to several physically identifiable reasons, including battery grid corrosion and sulphation (i.e., the growth of larger, insulating lead sulfate crystals that can no longer be used effectively as active material). FIG. 5 depicts values for high frequency resistance, Ro plotted as a function of battery useful life, for an exemplary battery system.

The determined value for Ro is preferably filtered (Step 40). The high frequency resistance Ro is normalized based upon a value for Ro(battery end of life), determined based upon ambient temperature T (Step 44). The parameter Ro(battery end of life) comprises a limiting value of Ro, determined, for example, when the battery is no longer capable of producing enough power to start the vehicle as a function of temperature. To predict remaining useful life of a battery, a normalized distance between the currently determined value of Ro and Ro(battery end of life) is computed (Step 44). Limiting values of Ro are determined based upon ambient temperature, and are preferably provided by the battery manufacturer, or, alternatively can be obtained by test results.

Normalizing Ro to determine a remaining useful life of a battery, i.e., state of health ('SOH'), can be calculated using a linear normalizing equation, shown in Eq. 11, below:

$$SOH = \frac{R_{o,limit} - R_o}{R_{o,limit} - R_{o,new}} * 100\% \quad [11]$$

For a newly installed battery, SOH is set to 100%. As the battery ages and resistance increases, the SOH decreases. Alternatively, the remaining useful life of a battery can be calculated using an exponential normalizing equation, shown in Eq. 12, below, which takes into account the non-linear nature of battery aging and useful life.

$$SOH = \exp\left[\frac{-\alpha(R_{o,limit} - R_{o,new})}{R_{o,limit} - R_o}\right] * 100\% \quad [12]$$

wherein $\alpha$ comprises a factor derived based upon real world data depicting exponential aging of the exemplary battery, an example of which is depicted in FIG. 5. The remaining useful life of the battery is communicated to an operator at next actuation of the system (Step 46), and operation continues (Step 52). The control module preferably shuts down thereafter.

When the battery age is less than a predetermined time value, e.g., N weeks (Step 42), the determined value for Ro at the ambient temperature T are added to a calibration table stored in memory of the control module, to form a baseline calibration for the new battery (Step 48) and the remaining useful life of the battery is indicated as 100%, and communicated to the operator at next actuation of the system (Step 50).

The invention has been described with specific reference to the preferred embodiments and modifications thereto. Further modifications and alterations may occur to others upon reading and understanding the specification. It is intended to include all such modifications and alterations insofar as they come within the scope of the invention.

Having thus described the invention, it is claimed:

1. Method for monitoring an electrical energy storage device, comprising:
    stabilizing the electrical energy storage device;
    cyclically applying an electrical load to the electrical energy storage device;
    monitoring state variables of the electrical energy storage device;
    determining a resistance of the electrical energy storage device; and,
    determining a remaining useful life parameter of the electrical energy storage device based upon the determined resistance.

2. The method of claim 1, wherein cyclically applying the electrical load to the electrical energy storage device comprises cyclically activating and deactivating a discrete electrical load.

3. The method of claim 2, wherein cyclically applying the discrete electrical load further comprises: selectively decreasing a cycle period for activating and deactivating the discrete electrical load.

4. Method for monitoring an electrical energy storage device, comprising:
    stabilizing the electrical energy storage device;
    cyclically activating and deactivating a discrete electrical load including executing a plurality of successive cyclical electrical load events each cyclical load event comprising a plurality of cycles of the discrete electrical load applied at a fixed frequency, wherein each successive cyclical electrical load event is executed at an increased frequency;
    monitoring state variables of the electrical energy storage device;
    determining a resistance of the electrical energy storage device; and determining a remaining useful life parameter of the electrical energy storage device based upon the determined resistance.

5. Method for monitoring an electrical energy storage device, comprising:
stabilizing the electrical energy storage device;
cyclically applying an electrical load to the electrical energy storage device;
monitoring state variables of the electrical energy storage device;
determining a resistance of the electrical energy storage device comprising estimating the resistance by recursively executing a parametric equation comprising a mathematical model of an electrical circuit representative of the electrical energy storage device based upon the monitored state variables of the electrical energy storage device; and
determining a remaining useful life parameter of the electrical energy storage device based upon the determined resistance.

6. Method for monitoring an electrical energy storage device, comprising:
stabilizing the electrical energy storage device;
cyclically applying an electrical load to the electrical energy storage device;
monitoring state variables of the electrical energy storage device;
determining a resistance of the electrical energy storage device; and
determining a remaining useful life parameter of the electrical energy storage device based upon the determined resistance comprising comparing the determined resistance and resistances of a new device and a low limit device.

7. The method of claim 6, further comprising comparing the determined resistance and the resistances of a new device and a low limit device based upon temperature.

8. Method for monitoring an electrical energy storage device, comprising:
stabilizing the electrical energy storage device comprising executing the method only after a delay of an elapsed period of time sufficient for the electrical energy storage device to achieve ambient temperature;
cyclically applying an electrical load to the electrical energy storage device;
monitoring state variables of the electrical energy storage device;
determining a resistance of the electrical energy storage device; and
determining a remaining useful life parameter of the electrical energy storage device based upon the determined resistance.

9. The method of claim 1, further comprising executing the method during a period in which the system is deactivated.

10. Method for monitoring a state of health of an electrical energy storage device for a system, comprising:
stabilizing the electrical energy storage device;
cyclically applying a discrete electrical load to the electrical energy storage device;
monitoring state variables of the electrical energy storage device;
determining a resistance of the electrical energy storage device; and,
comparing the determined resistance and resistances of a new device and a low limit device based upon temperature.

11. The method of claim 10, wherein cyclically applying a discrete electrical load to the electrical energy storage device comprises cyclically activating and deactivating the electrical load at decreasing cycle periods.

12. The method of claim 11, wherein cyclically activating and deactivating the electrical load at decreasing cycle periods comprises cycle periods ranging from about twenty seconds to less than five seconds.

13. Method for monitoring a state of health of an electrical energy storage device for a system, comprising:
stabilizing the electrical energy storage device;
cyclically applying a discrete electrical load to the electrical energy storage device;
monitoring state variables of the electrical energy storage device;
determining a resistance of the electrical energy storage device comprising recursively solving a parametric equation representative of the electrical energy storage device based upon the monitored state variables of the electrical energy storage device; and
comparing the determined resistance and resistances of a new device and a low limit device based upon temperature.

14. The method of claim 13, wherein the monitored state variables comprise voltage and current.

15. Method for monitoring a state of health of an electrical energy storage device for a system, comprising:
stabilizing the electrical energy storage device;
cyclically applying a discrete electrical load to the electrical energy storage device;
monitoring state variables of the electrical energy storage device;
determining a resistance of the electrical energy storage device; and
comparing the determined resistance and resistances of a new device and a low limit device based upon temperature, including linearly comparing the determined resistance and resistances of the new device and the low limit device.

16. Method for monitoring a state of health of an electrical energy storage device for a system, comprising:
stabilizing the electrical energy storage device;
cyclically applying a discrete electrical load to the electrical energy storage device;
monitoring state variables of the electrical energy storage device;
determining a resistance of the electrical energy storage device; and
comparing the determined resistance and resistances of a new device and a low limit device based upon temperature including exponentially comparing the determined resistance and resistances of the new device and the low limit device.

17. Method for monitoring a state of health of an electrical energy storage device for a system, comprising:
stabilizing the electrical energy storage device including deactivating the system for a period effective to stabilize temperature of the electrical energy storage device;
cyclically applying a discrete electrical load to the electrical energy storage device;
monitoring state variables of the electrical energy storage device;
determining a resistance of the electrical energy storage device; and
comparing the determined resistance and resistances of a new device and a low limit device based upon temperature.

18. Article of manufacture, comprising a storage medium having machine-executable code encoded therein effective to monitor a state of health of an electrical energy storage device for a system, the code comprising:
   code to stabilize the electrical energy storage device;
   code to cyclically apply a discrete electrical load to the electrical energy storage device;
   code to monitor state variables of the electrical energy storage device;
   code to determine a resistance of the electrical energy storage device; and,
   code to determine a remaining useful life parameter of the electrical energy storage device based upon the determined resistance.

19. The article of claim 18, wherein code to selectively apply a discrete electrical load to the electrical energy storage device comprises code to cyclically activate and deactivate a discrete electrical load.

20. The article of claim 18, wherein the code to determine a resistance of the electrical energy storage device comprises code to recursively execute an equation effective to estimate parameters of the electrical energy storage device based upon the monitored state variables of the electrical energy storage device.

* * * * *